(12) United States Patent
Matoba et al.

(10) Patent No.: US 7,964,758 B2
(45) Date of Patent: Jun. 21, 2011

(54) PROCESS FOR PRODUCTION OF 2-(SUBSTITUTED PHENYL)-3,3,3-TRIFLUOROPROPENE COMPOUND

(75) Inventors: Kazutaka Matoba, Funabashi (JP); Takashi Mizukoshi, Funabashi (JP); Yuji Moriyama, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 340 days.

(21) Appl. No.: 12/223,657

(22) PCT Filed: Feb. 13, 2007

(86) PCT No.: PCT/JP2007/052510
§ 371 (c)(1),
(2), (4) Date: Aug. 6, 2008

(87) PCT Pub. No.: WO2007/094313
PCT Pub. Date: Aug. 23, 2007

(65) Prior Publication Data
US 2010/0160683 A1 Jun. 24, 2010

(30) Foreign Application Priority Data
Feb. 13, 2006 (JP) ................... 2006-035401

(51) Int. Cl.
*C07C 17/32* (2006.01)
(52) U.S. Cl. ........................ 570/142; 570/128
(58) Field of Classification Search ........... 570/128, 570/142; 564/218; 568/628
See application file for complete search history.

(56) References Cited

U.S. PATENT DOCUMENTS

| 6,218,564 | B1 | 4/2001 | Monteith |
| 2006/0122398 | A1 | 6/2006 | Karch et al. |

FOREIGN PATENT DOCUMENTS

| CN | 1051911 A | 6/1991 |
| CN | 1263084 A | 8/2000 |
| CN | 1293197 A | 5/2001 |
| GB | 2 197 313 A | 5/1988 |
| JP | A-2001-501963 | 2/2001 |
| JP | A-2001-089402 | 4/2001 |
| JP | A-2005-008578 | 1/2005 |
| JP | A-2005-534711 | 11/2005 |
| WO | WO 2005/085216 | * 9/2005 |

OTHER PUBLICATIONS

Casreact: 2005(Corresponding to WO 2005/085216).*
Rui-Qi et al., "A novel and convenient synthetic method for producing α-(trifluoromethyl) styrenes (3)", Journal of Fluorine Chemistry, vol. 95, pp. 167-170, 1999.
Jiang et al., "α-(Trifluoromethyl) ethenyl boronic acid as a useful trifluoromethyl containing building block. Preparation and palladium-catalysed coupling with aryl halides",Tetrahedron Letters, vol. 42, pp. 4083-4085, 2001. Mori et al., "4-Difluoromethylated Quinoline Synthesis via Intramolecular $S_N2'$ Reaction of α-Trifluoromethylstyrenes Bearing Imine Moieties", Chemistry Letters, vol. 33, No. 9, pp. 1206-1207, 2004.
Lebel et al., "Highly Chemoselective Rhodium-Catalyzed Methylenation of Fluorine-Containing Ketones", Organic Letters; vol. 4, No. 10, pp. 1671-1674, 2002.
Paratian et al., "Electrosynthesis of (trifluoromethyl) copper complexes from bromotrifluoromethane: reactivities with various organic halides", Journal of Organometallic Chemistry, vol. 489, pp. 137-143 1995.
Nader et al., "A Novel Fluoride Ion Mediated Olefination of Electron-Deficient Aryl Ketone by Alkanesulfonyl Halides", Journal of Organic Chemistry, vol. 59, No. 10 pp. 2898-2901, 1994.

* cited by examiner

*Primary Examiner* — Shailendra Kumar
(74) *Attorney, Agent, or Firm* — Oliff & Berridge, PLC

(57) ABSTRACT

There is provided a novel process for production of a 2-(substituted phenyl) -3,3,3-trifluoropropene.

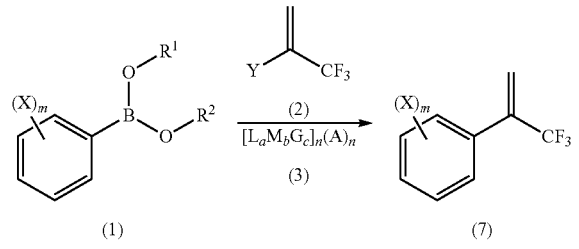

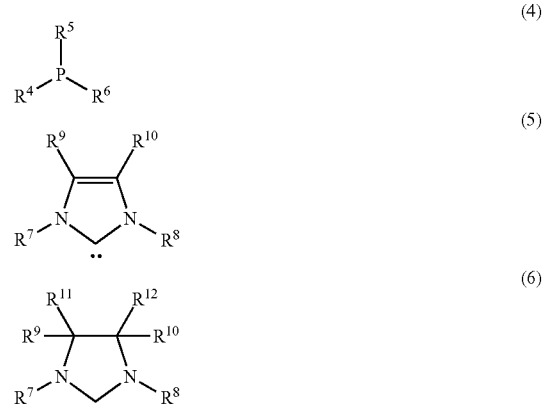

Disclosed is a process for production of a 2-(substituted phenyl)-3,3,3-trifluoropropene compound represented by the formula (7) or a salt thereof The process comprises reacting a compound represented by the formula (1) (X is an alkyl group, etc.) with a compound represented by the formula (2) (Y is a halogen atom, etc.) in the presence of a catalyst represented by the formula (3) (M is an ion of a metal belonging to Group 10 on the elementary periodic table which has an oxidation state number of 1 to 8; G is a unidentate or multidentate ligand; L is a phosphine compound represented by the formula (4) which is bound to the center metal M or is a carbene selected from those represented by the formulae (5) and (6), provided that L's may be same as or different from one another when a is 2 to 5; A represents a univalently or multivalently charged anion; b represents an integer of 1 to 3; a represents an integer of 1 to 5·b; c represents 0 or an integer of 1 to 4·b; and n represents an integer of 1 to 6).

6 Claims, No Drawings

PROCESS FOR PRODUCTION OF 2-(SUBSTITUTED PHENYL)-3,3,3-TRIFLUOROPROPENE COMPOUND

This application is a 371 of PCT/JP2007/052510, filed Feb. 13, 2007.

TECHNICAL FIELD

The present invention relates to a process for production of a 2-(substituted phenyl)-3,3,3-trifluoropropene compound useful as a medicine/pesticide or a production intermediate thereof, or a monomer for a functional polymer.

BACKGROUND ART

Conventionally, as a process for production of a 2-(substituted phenyl)-3,3,3-trifluoropropene compound, Patent Documents 1 to 4 and Non-patent Documents 1 to 5, for example, are known. However, there is not a process capable of producing industrially the above compound and capable of obtaining the above compound in high yield, and thus it is not necessarily a satisfactory circumstance. In addition, a synthesis example using the so-called Suzuki-Miyaura coupling reaction in which the reaction is effected using a substituted phenylboronic acid, a substituted phenylboronic ester or a substituted phenylboronic acid salt as a raw material in the presence of a Group 10 transition metal catalyst, is described in Patent Document 2 and Non-patent Document 3. Among them in Patent Document 2, the yield is not so high as 49 to 73% and further, it is so limited that a substituent in a phenyl group surely contains a carboxyamide group. On the other hand, in Non-patent Document 3, depending on the substituent of a phenylboronic acid, the yield remains at around 70% and further, an arsenic compound is used as a ligand, which is impracticable.

[Patent Document 1]
 Chinese Patent No. 1293197 (2001)
[Patent Document 2]
 Chinese Patent No. 1263084 (2000)
[Patent Document 3]
 Chinese Patent No. 1051911 (1991)
[Patent Document 4]
 United Kingdom Patent No. 2197313 (1988)
[Non-patent Document 1]
 Chemistry Letters (2004), Vol. 33 (9), p 1206
[Non-patent Document 2]
 Organic Letters (2002), Vol. 4 (10), p 1671
[Non-patent Document 3]
 Journal of Fluorine Chemistry (1999), Vol. 95, p 167
[Non-patent Document 4]
 Journal of Organometallic Chemistry (1995), Vol. 489 (1-2), p 137
[Non-patent Document 5]
 Journal of Organic Chemistry (1994), Vol. 59 (10), p 2898

DISCLOSURE OF THE INVENTION

Problems to be Solved by the Invention

As described above, an existing process leaves room for improvement as a process for production of a 2-(substituted phenyl)-3,3,3-trifluoropropene compound in terms of the yield and terms of the commercialization of the industrial production thereof.

Means for Solving the Problem

In the above-mentioned situation, the present inventors have made keen examinations and as the result, it has been found that in the production of a 2-(substituted phenyl)-3,3,3-trifluoropropene compound, by using a certain kind of catalyst, the catalyst can be reduced to such an extent that the industrial production in high yield and in high selectivity becomes possible. Based on this novel finding, the invention has been completed.

That is, the present invention is as follows.

[1] A process for production of a 2-(substituted phenyl)-3,3,3-trifluoropropene compound or a salt thereof, the compound being represented by the formula (7):

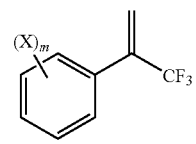

(7)

wherein X represents a halogen atom, a cyano group, a nitro group, —SF$_5$, a C$_1$-C$_6$ alkyl group, a C$_1$-C$_6$ haloalkyl group, a hydroxy (C$_1$-C$_6$) haloalkyl group, a C$_1$-C$_6$ alkoxy (C$_1$-C$_6$) haloalkyl group, a C$_1$-C$_6$ haloalkoxy (C$_1$-C$_6$) haloalkyl group, a C$_3$-C$_8$ halocycloalkyl group, —OR$^3$, —OSO$_2$R$^3$ or —S(O)$_r$R$^3$; and m represents an integer of 1 to 5 and when m represents 2 or more, each of Xs may be identical to or different from each other, by reacting a substituted phenylboronic acid or a substituted phenylboronic ester or a substituted phenylboronic acid salt represented by the formula (1):

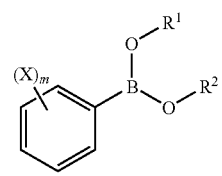

(1)

wherein X and m represent the same meanings as those above described; R$^1$ and R$^2$ may be identical to or different from each other and represent a hydrogen atom or an alkyl group, or a divalent hydrocarbon residue formed by R$^1$ and R$^2$ together in which the terminals of R$^1$ and R$^2$ are bonded to each other; R$^3$ represents a C$_1$-C$_6$ alkyl group, a C$_1$-C$_6$ haloalkyl group or a C$_1$-C$_3$ haloalkoxy (C$_1$-C$_3$) haloalkyl group; and r represents an integer of 0 to 2, with a 2-halogen-3,3,3-trifluoropropene compound or salt thereof, the compound being represented by the formula (2):

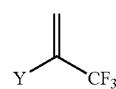

(2)

wherein Y represents a halogen atom, in the presence of a complex catalyst represented by the formula (3):

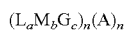

$(L_aM_bG_c)_n(A)_n$   (3)

wherein M represents as a central atom, an ion of a metal belonging to Group 10 on the elementary periodic table in an oxidation state number of 1 to 8; G represents a unidentate or multidentate charged or uncharged ligand bonded to the central atom M; L is bonded as a ligand to the central atom M, and represents a phosphine compound represented by the formula (4):

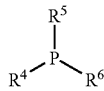
(4)

wherein each of $R^4$, $R^5$ and $R^6$ may be identical to or different from each other and represent a hydrogen atom, a $C_1$-$C_6$ alkyl group, a $C_3$-$C_{18}$ monocyclic or polycyclic cycloalkyl group or a $C_6$-$C_{14}$ aryl group which may be substituted by a substituent such as a di-($C_1$-$C_6$ alkyl) amino group, a $C_1$-$C_6$ alkoxyl group and an aryl group which may be substituted by a substituent such as a di-($C_1$-$C_6$ alkyl) amino group and a $C_1$-$C_6$ alkoxyl group, or a carbene represented by the formula (5):

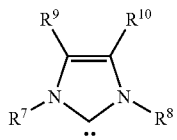
(5)

or by the formula (6):

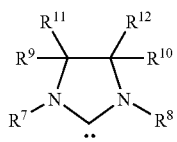
(6)

wherein each of $R^7$ and $R^8$ may be identical to or different from each other and represent a linear or branched $C_1$-$C_7$ alkyl group, a monocyclic or polycyclic $C_3$-$C_{18}$ cycloalkyl group or an aryl group having 6 to 14 carbon atoms which may be substituted by a substituent such as a linear or branched $C_1$-$C_7$ alkyl group and a monocyclic or polycyclic $C_3$-$C_{18}$ cycloalkyl group; each of $R^9$, $R^{10}$, $R^{11}$ and $R^{12}$ may be identical to or different from each other, may be also a hydrogen atom, and represent a linear or branched $C_1$-$C_7$ alkyl group, a monocyclic or polycyclic $C_3$-$C_{18}$ cycloalkyl group, an aryl group which is optionally substituted by a linear or branched $C_1$-$C_7$ alkyl group and having 6 to 14 carbon atoms, a linear or branched $C_1$-$C_7$ alkoxy group, or a linear or branched $C_1$-$C_7$ alkylthio group; and $R^7$ and $R^9$, $R^8$ and $R^{10}$, $R^7$, $R^9$ and $R^{11}$, or $R^8$, $R^{10}$ and $R^{12}$ may form together a condensed ring, in which when a represents 2 to 15, each of Ls may be identical to or different from each other with proviso that all Ls do not represent simultaneously triphenylphosphine, A represents a univalently or multivalently charged anion; b represents any integer of 1 to 3; a represents an integer produced by multiplying any integer of 1 to 5 by the above integer b; c represents 0 or represents an integer produced by multiplying an integer of 1 to 4 by the above b; and n represents any integer of 1 to 6.

[2] In the process for production according to [1], the X represents a halogen atom or a $C_1$-$C_4$ haloalkyl group and m represents an integer of 1 to 3, in which when m represents 2 or 3, each of Xs may be identical to or different from each other.

[3] In the process for production according to [1], at least one of the Ls represents a carbene represented by the formula (5) or (6).

[4] In the process for production according to [1], at least one of the Ls represents a carbene represented by the formula (5) or (6), and each of $R^7$ and $R^8$ represents 2,4,6-trimethylphenyl group, 2,6-diisopropylphenyl group, 2,6-diisopropyl-4-methylphenyl group, 1-adamantyl group, a tert-butyl group, a cyclohexyl group, a tolyl group, or a xylyl group; and $R^9$, $R^{10}$, $R^{11}$ and $R^{12}$ represent a hydrogen atom.

[5] In the process for production according to [1], at least one of the Ls represents a phosphine compound represented by the formula (4), and at least one of $R^4$, $R^5$ and $R^6$ represents an adamantyl group, a norbornyl group, a tert-butyl group or a cyclohexyl group.

Effects of the Invention

According to the process for production of the present invention, a 2-(substituted phenyl)-3,3,3-trifluoropropene compound important as a production intermediate for a medicine and pesticide and a functional material can be produced in high efficiency and high selectivity and further during the production, a used catalyst can be reduced to an extremely small amount, so that a valuable process for the industrial production thereof can be provided.

BEST MODES FOR CARRYING OUT THE INVENTION

Hereinafter, the present invention will be more specifically described.

Examples of the compound capable of being converted into an acid addition salt by a common procedure among the compounds encompassed in the present invention include: salts of a halogenated hydracid such as hydrofluoric acid, hydrochloric acid, hydrobromic acid and hydriodic acid; salts of an inorganic acid such as nitric acid, sulfuric acid, phosphoric acid, chloric acid and perchloric acid; salts of a sulfonic acid such as methanesulfonic acid, ethanesulfonic acid, trifluoromethanesulfonic acid, benzenesulfonic acid and p-toluenesulfonic acid; salts of a carboxylic acid such as formic acid, acetic acid, propionic acid, trifluoroacetic acid, fumaric acid, tartaric acid, oxalic acid, maleic acid, malic acid, succinic acid, benzoic acid, mandelic acid, ascorbic acid, lactic acid, gluconic acid and citric acid; and salts of an amino acid such as glutamic acid and aspartic acid.

On the other hand, examples of the compound capable of being converted into a metal salt by a common procedure among the compounds encompassed in the present invention include: salts of an alkali metal such as lithium, sodium and potassium; salts of an alkaline earth metal such as calcium, barium and magnesium; and salts of aluminum.

Next, specific examples of each substituent shown in the present specification are shown as follows. Here, n- means normal, i- means iso, s- means secondary and t- means tertiary, respectively; o- means ortho, m- means meta and p- means para; and Ph means phenyl.

Examples of the halogen atom in the compound of the present invention include a fluorine atom, a chlorine atom, a bromine atom and an iodine atom. Here, the notation of "Halo" in the present specification represents also these halogen atoms.

The notation of $C_a$-$C_b$ alkyl group in the present specification represents a linear or branched hydrocarbon group having a carbon atom number of a to b and specific examples thereof include a methyl group, an ethyl group, an n-propyl group, an i-propyl group, an n-butyl group, an i-butyl group, an s-butyl group, a t-butyl group, an n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a 1-methylpentyl group, a 2-methylpentyl group, a 1,1-dimethylbutyl group, an 1,3-dimethylbutyl group, a heptyl group, an octyl group, a nonyl group, a decyl group, an undecyl group and a dodecyl group. Each may be selected from a range of a specified carbon atom number.

The notation of $C_a$-$C_b$ haloalkyl group in the present specification represents a linear or branched hydrocarbon group having a carbon atom number of a to b in which hydrogen atoms bonded to a carbon atom are arbitrarily substituted by a halogen atom and at this time, when the hydrogen atoms are substituted by 2 or more halogen atoms, these halogen atoms may be identical to or different from each other. Specific examples of such a hydrocarbon group include a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a dibromofluoromethyl group, a 2-fluoroethyl group, a 2-chloroethyl group, a 2-bromoethyl group, a 2,2-difluoroethyl group, a 2-chloro-2-fluoroethyl group, a 2,2-dichloroethyl group, a 2-bromo-2-fluoroethyl group, a 2,2,2-trifluoroethyl group, a 2-chloro-2,2-difluoroethyl group, a 2,2-dichloro-2-fluoroethyl group, a 2,2,2-trichloroethyl group, a 2-bromo-2,2-difluoroethyl group, a 2-bromo-2-chloro-2-fluoroethyl group, a 2-bromo-2,2-dichloroethyl group, a 1,1,2,2-tetrafluoroethyl group, a pentafluoroethyl group, a 1-chloro-1,2,2,2-tetrafluoroethyl group, a 2-chloro-1,1,2,2-tetrafluoroethyl group, a 1,2-dichloro-1,2,2,2-trifluoroethyl group, a 2-bromo-1,1,2,2-tetrafluoroethyl group, a 2-fluoropropyl group, a 2-chloropropyl group, a 2-bromopropyl group, a 2-chloro-2-fluoropropyl group, a 2,3-dichloropropyl group, a 2-bromo-3-fluoropropyl group, a 3-bromo-2-chloropropyl group, a 2,3-dibromopropyl group, a 3,3,3-trifluoropropyl group, a 3-bromo-3,3-difluoropropyl group, a 2,2,3,3-tetrafluoropropyl group, a 2-chloro-3,3,3-trifluoropropyl group, a 2,2,3,3,3-pentafluoropropyl group, a 1,1,2,3,3,3-hexafluoropropyl group, a heptafluoropropyl group, a 2,3-dichloro-1,1,2,3,3-pentafluoropropyl group, a 2-fluoro-1-methylethyl group, a 2-chloro-1-methylethyl group, a 2-bromo-1-methylethyl group, a 2,2,2-trifluoro-1-(trifluoromethyl)ethyl group, a 1,2,2,2-tetrafluoro-1-(trifluoromethyl)ethyl group, a 2-fluoro-butyl group, a 2-chlorobutyl group, a 2,2,3,3,4,4-hexafluorobutyl group, a 2,2,3,4,4,4-hexafluorobutyl group, a 2,3,3,4,4,4-hexafluorobutyl group, a 2,2,3,3,4,4,4-heptafluorobutyl group, a 1,1,2,2,3,3,4,4-octafluorobutyl group, a nonafluorobutyl group, a 4-chloro-1,1,2,2,3,3,4,4-octafluorobutyl group, a 2-fluoro-2-methylpropyl group, an 1,2,2,3,3,3-hexafluoro-1-(trifluoromethyl)propyl group, a 2-chloro-1,1-dimethylethyl group, a 2-bromo-1,1-dimethylethyl group, a 5-chloro-2,2,3,4,4,5,5-heptafluoropentyl group and a tridecafluorohexyl group. Each may be selected from a range of a specified carbon atom number.

The notation of $C_a$-$C_b$ halocycloalkyl group in the present specification represents a cyclic hydrocarbon group having a carbon atom number of a to b in which hydrogen atoms bonded to a carbon atom are arbitrarily substituted by a halogen atom which can form a 3- to 6-membered monocyclic or compound cyclic structure. In addition, each ring may be arbitrarily substituted with an alkyl group within a specified range of the carbon atom number, and either the ring structure portion or the side chain portion may be substituted with a halogen atom or both of them may be. Further, when each ring is substituted with 2 or more halogen atoms, these halogen atoms may be identical to or different from each other. Specific examples of such a cyclic hydrocarbon group include a 2,2-difluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 2,2,3,3-tetrafluorocyclobutyl group, a 2-(trifluoromethyl)cyclohexyl group, a 3-(trifluoromethyl)cyclohexyl group and a 4-(trifluoromethyl)cyclohexyl group. Each may be selected from a range of a specified carbon atom number.

The notation of $C_a$-$C_b$ alkoxy group in the present specification represents an alkyl-O— group having a carbon atom number of a to b and having the above-described meaning and specific examples thereof include a methoxy group, an ethoxy group, a n-propyloxy group, an i-propyloxy group, a n-butyloxy group, an i-butyloxy group, an s-butyloxy group, a t-butyloxy group, a n-pentyloxy group and a n-hexyloxy group. Each may be selected from a range of a specified carbon atom number.

The notation of $C_a$-$C_b$ haloalkoxy group in the present specification represents a haloalkyl-O— group having a carbon atom number of a to b and having the above-described meaning and specific examples thereof include a difluoromethoxy group, a trifluoromethoxy group, a chlorodifluoromethoxy group, a bromodifluoromethoxy group, a 2-fluoroethoxy group, a 2-chloroethoxy group, a 2,2,2-trifluoroethoxy group, an 1,1,2,2-tetrafluoroethoxy group, a 2-chloro-1,1,2-trifluoroethoxy group, a 2-bromo-1,1,2-trifluoroethoxy group, a pentafluoroethoxy group, a 2,2-dichloro-1,1,2-trifluoroethoxy group, a 2,2,2-trichloro-1,1-difluoroethoxy group, a 2-bromo-1,1,2,2-tetrafluoroethoxy group, a 2,2,3,3-tetrafluoropropyloxy group, a 1,1,2,3,3,3-hexafluoropropyloxy group, a 2,2,2-trifluoro-1-(trifluoromethyl)ethoxy group, a heptafluoropropyloxy group and a 2-bromo-1,1,2,3,3,3-hexafluoropropyloxy group. Each may be selected from a range of a specified carbon atom number.

The notation of hydroxy ($C_d$-$C_e$) haloalkyl group, $C_a$-$C_b$ alkoxy ($C_d$-$C_e$)haloalkyl group or $C_a$-$C_b$ haloalkoxy ($C_d$-$C_e$) haloalkyl group in the present specification represents a haloalkyl group having a carbon atom number of d to e and having the above-described meaning in which a hydrogen or halogen atom bonded to a carbon atom is arbitrarily substituted by an arbitrary $C_a$-$C_b$ alkoxy group and $C_a$-$C_b$ haloalkoxy group which each of them have the above-described meaning or hydroxy group, and specific examples thereof include a 2,2,2-trifluoro-1-hydroxy-1-(trifluoromethyl)ethyl group, a difluoro(methoxy)methyl group, a 2,2,2-trifluoro-1-methoxy-1-(trifluoromethyl)ethyl group, a difluoro(2,2,2-trifluoroethoxy)methyl group, a 2,2,2-trifluoro-1-(2,2,2-trifluoroethoxy)-1-(trifluoromethyl)ethyl group, a 3-(1,2-dichloro-1,2,2-trifluoroethoxy)-1,1,2,2,3,3 hexafluoro propyl group. Each may be selected from a range of a specified carbon atom number.

Examples of the notation of aryl group in the present specification include a phenyl group, a naphthyl group, an anthranil group, a phenanthrene group and a metallocene group such as a ferrocene group.

In the formula (1), $R^1$ and $R^2$ may be identical to or different from each other and represent a hydrogen atom, an alkyl group or a divalent hydrocarbon residue formed by $R^1$ and $R^2$ together in which the terminals of $R^1$ and $R^2$ are bonded to each other. As the alkyl group, there can be mentioned a linear or branched alkyl group having a carbon atom number of 1 to 6, preferably 1 to 4 and specific examples thereof include a methyl group, an ethyl group, an n-propyl group, an i-propyl group, an n-butyl group and a t-butyl group. Preferred examples of the divalent hydrocarbon residue formed by $R^1$ and $R^2$ together in which the terminals of $R^1$ and $R^2$ are bonded to each other include a group forming with an oxygen atom and a boron atom together a 5- or 6-membered ring and specific examples thereof include an alkylene group such as an ethylene group, a propylene group, a 2,3-dimethylbutane-2,3-diyl group and a 2,2-dimethylpropane-1,3-diyl group; an o-phenylene group; and a methyl -o-phenylene group. Among them, preferred is a 2,3-dimethylbutane-2,3-diyl group.

X represents a halogen atom, a cyano group, a nitro group, —$SF_5$, a $C_1$-$C_6$ alkyl group, a $C_1$-$C_6$ haloalkyl group, a hydroxy($C_1$-$C_6$)haloalkyl group, a $C_1$-$C_6$ alkoxy($C_1$-$C_6$)haloalkyl group, a $C_1$-$C_6$ haloalkoxy($C_1$-$C_6$)haloalkyl group, a $C_3$-$C_8$ halocycloalkyl group, —$OR^3$, —$OSO_2R^3$ or —$S(O)_r$ $R^3$, and when m represents 2 or more each of Xs may be identical to or different from each other. $R^3$ represents a $C_1$-$C_6$ alkyl group, a $C_1$-$C_6$ haloalkyl group or a $C_1$-$C_3$ haloalkoxy ($C_1$-$C_3$) haloalkyl group; and r represents an integer of 0 to 2. Further, X is preferably a halogen atom and a $C_1$-$C_4$ haloalkyl group, more preferably a chlorine atom, a bromine atom, an iodine atom and a trifluoromethyl group. At this time, when m representing the number of the substituent represented by X represents an integer of 2 or more, each of Xs may be identical to or different from each other.

In the compounds encompassed in the present invention, m representing the number of the substituent represented by X is preferably 1, 2 and 3.

In the formula (1), the position of the substituent represented by X is more preferably a meta position or para position relative to a binding position of a carbon atom to which a boron atom is bonded. In the formula (7), the position of the substituent represented by X is more preferably a meta position or para position relative to a binding position of a carbon atom to which a 3,3,3-trifluoropropene-2-yl group is bonded.

Further, the substituted phenylboronic acid compound may be formed, for example as a dehydration condensation product represented by the formula (8):

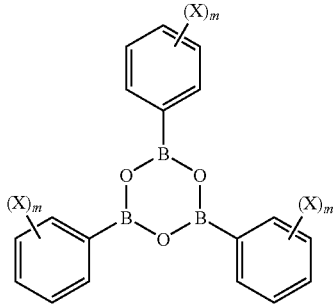

(8)

wherein X and m represent the same meanings as those above described.

In the formula (2), Y represents a halogen atom and is preferably a bromine atom and specific examples of the 2-halogen-3,3,3-trifluoropropene compound include 2-bromo-3,3,3-trifluoropropene.

As described in Non-patent Document 3, 2-bromo-3,3,3-trifluoropropene can be easily synthesized by subjecting 1,2-dibromo-3,3,3-trifluoropropane to a dehydrobromination in the presence of a base and can be then continuously subjected to the Suzuki-Miyaura coupling reaction. In other words, as a starting raw material for obtaining a 2-(substituted phenyl)-3,3,3-trifluoropropene compound, 1,2-dibromo-3,3,3-trifluoropropane can be used instead of 2-bromo-3,3,3-trifluoropropene.

Examples of the solvent capable of being used in the reaction of the present invention include water; nitriles such as acetonitrile; aprotic polar solvents such as N,N-dimethylformamide, dimethylsulfoxide or N-methylpyrrolidone; ethers such as dimethoxyethane, tetrahydrofuran, tert-butyl methyl ether, cyclopentyl methyl ether or 1,4-dioxane; alcohols such as methanol, ethanol, n-propanol, i-propanol, n-butanol or t-butanol; aromatic hydrocarbons such as benzene, toluene or xylene; and aliphatic hydrocarbons such as n-hexane, n-heptane or cyclohexane. Among them, preferred are water, nitriles and ethers, particularly preferred are water, acetonitrile, tetrahydrofuran and 1,4-dioxane. These solvents may be used individually or in combination of 2 or more kinds.

The used amount of such solvents is not particularly limited, however, is normally 0.1 to 100 parts by weight, preferably 1 to 50 parts by weight, particularly preferably 2 to 15 parts by weight relative to 1 part by weight of substituted phenylboronic acid compounds or substituted phenylboronic acid esters. The used amount of a 2-halogen-3,3,3-trifluoropropene compound represented by the formula (2) is normally 0.5 to 100 times mole, preferably 0.7 to 10 times mole, particularly preferably 1 to 1.5 times mole relative to 1 mole of substituted phenylboronic acid compounds or substituted phenylboronic acid esters.

In the formula (3), M is an ion of a metal belonging to Group 10 on the elementary periodic table in an oxidation state number of 1 to 8 as a central atom and is preferably an ion of Ni or Pd in an oxidation state number of 1 to 8, more preferably an ion of Pd in an oxidation state number of 1 to 8.

In the formula (3), L is a phosphine represented by the formula (4) or a carbene represented by the formula (5) or formula (6) which are bonded to the central atom M as a ligand. Specific examples of the phosphine include tri-n-propyl phosphine, tri-i-propyl phosphine, tri-n-butyl phosphine, tri-s-butyl phosphine, tri-t-butyl phosphine, tricyclohexyl phosphine, o-biphenyl-di-t-butyl phosphine, o-biphenyl-dicyclohexyl phosphine, tri-o-tolyl phosphine, di-t-butylmethyl phosphine, di-t-butylferrocenyl phosphine, di-1-adamantyl-t-butyl phosphine, di-1-adamantyl -o-biphenyl phosphine, 1-adamantyl-di-t-butyl phosphine, di-1-adamantyl phosphine, di-1-norbornyl phosphine, dicyclohexyl-o-ferrocenyl phosphine. Specific examples of the carbene include 1,3-bis-(mesityl)imidazol-2-ylidene (IMes), 1,3-bis-(2,6-diisopropylphenyl)imidazol-2-ylidene (IPr), 1,3-bis-(adamantyl) imidazol-2-ylidene (IAd), 1,3-bis-(cyclohexyl) imidazol-2-ylidene (ICy), 1,3-bis-(2,6-dimethylphenyl) imidazol-2-ylidene (IXy), 1,3-bis-(tolyl)imidazol-2-ylidene (ITol), dispiro(cyclohexane-1,3'(2'H)-imidazo(5,1-b:4, 3-b') bisoxazol(4)ium-7'(8'H),1"-cyclohexane)carbene (IBiox6), 1,3-bis-(mesityl)-4,5-dihydro imidazol-2-ylidene (SIMes), 1,3-bis-(2,6-diisopropylphenyl)-4,5-dihydroimidazol-2-ylidene (SIPr), 1,3-bis-(adamantyl)-4,5-dihydroimidazol-2-ylidene (SIAd), 1,3-bis-(cyclohexyl)-4,5-dihydroimidazol-2-ylidene (SICy), 1,3-bis-(2,6-dimethylphenyl)-4,5- dihydroimidazol-2-ylidene (SIXy) and 1,3-bis-(tolyl)-4,5-dihydroimidazol-2-ylidene (SITol).

In the formula (3), G is a unidentate or multidentate ligand and is preferably a hydrogen atom or a hydrogen ion, a halogen atom or a halogen ion, a pseudo halide, a carboxylate ion, a sulfonate ion, an amide group, an alcoholate group, an acetylacetonate group, carbon monoxide, an alkyl group having 1 to 7 carbon atoms, nitrogen monoxide, a nitrile group, an isonitrile group, a mono- and di-olefin group, an alkyne group and π-aromatic group.

In the formula (3), a is preferably 1 or 2, b is preferably 1, n is preferably a number of 1 to 3. A is preferably a halide-, a pseudo halide-, a tetraphenylborate-, a tetrafluoroborate-, a hexafluorophosphate-, a hexafluoroantimonate-, a carboxylate ion (particularly an acetate ion), and a metal complex anion such as a tetracarbonyl-cobaltate, a hexafluoroferrate (III), a tetrachloroferrate (III), a tetrachloroaluminate or a tetrachloropalladate (II).

As the catalyst according to the present invention, either a catalyst is prepared beforehand by combining a metal belonging to Group 10 on the elementary periodic table and a ligand such as the L and an isolated metal complex can be used, or a catalyst prepared by stirring a salt of a metal belonging to Group 10 on the elementary periodic table and a ligand such as the L or a ligand precursor in a solvent can be used.

When the ligand is a carbene, specific examples of the ligand precursor include 1,3-bis-(mesityl)imidazolium chloride (IMes.HCl), 1,3-bis-(2,6-diisopropylphenyl)imidazolium chloride (IPr.HCl), 1,3-bis-(adamantly)imidazolium chloride (IAd.HCl), 1,3-bis-(cyclohexyl)imidazolium chloride (ICy.HCl), 1,3-bis-(2,6-dimethylphenyl)imidazolium chloride (IXy.HCl), 1,3-bis-(tolyl)imidazolium chloride (ITol.HCl), dispiro(cyclohexane-1,3'(2'H)-imidazo(5,1-b:4,3-b')bisoxazol(4)ium-7'(8'H), 1"-cyclohexane)trifluoromethanesulfonic acid salt (IBiox6.HOTf), 1,3-bis-(mesity1)-4,5-dihydroimidazolium chloride (SIMes.HCl), 1,3-bis-(2,6-diisopropylphenyl)-4,5-dihydroimidazolium chloride (SIPr.HCl), 1,3-bis-(adamantyl)-4,5-dihydroimidazolium chloride (SIAd.HCl), 1,3-bis-(cyclohexyl)-4,5-dihydroimidazolium chloride (SICy.HCl), 1,3-bis-(2,6-dimethylphenyl)-4,5-dihydroimidazolium chloride (SIXy.HCl), 1,3-bis-(tolyl)-4,5-dihydroimidazolium chloride (SITol.HCl), 1,3-bis-(mesityl)-4,5-dihydroimidazolium tetrafluoroborate (SIMes.HBF$_4$), 1,3-bis-(2,6-diisopropylphenyl)-4,5-dihydroimidazolium tetrafluoroborate (SIPr.HBF$_4$) and 1,3-bis-(adamantyl)-4,5-dihydroimidazolium tetrafluoroborate (SIAd.HBF$_4$).

It is advantageous that the used amount of the catalyst is normally 0.00000001 to 1 time mole, preferably 0.000001 to 0.1 time mole relative to 1 mole of substituted phenylboronic acid compounds or substituted phenylboronic esters.

As the base according to the present invention, heretofore known inorganic bases or organic bases can be widely used. Examples of the inorganic base include an alkali metal carbonate such as potassium carbonate, sodium carbonate, lithium carbonate or cesium carbonate; an alkali metal hydroxide such as sodium hydroxide, potassium hydroxide, lithium hydroxide or cesium hydroxide; an alkaline earth metal carbonate such as magnesium carbonate or calcium carbonate; an alkaline earth metal hydroxide such as magnesium hydroxide or calcium hydroxide; a hydrogen carbonate such as sodium hydrogen carbonate or potassium hydrogen carbonate; a phosphate such as sodium phosphate or potassium phosphate; a hydrogen phosphate such as potassium hydrogen phosphate or sodium hydrogen phosphate; or a fluoride such as potassium fluoride or sodium fluoride. Examples of the organic base include triethylamine, diisopropylethylamine, tri-n-butylamine, diethylamine, diisopropylamine, methylmorpholine, morpholine and diethylaniline.

It is advantageous that the amount of such a base is normally 1 to 10 times mole, preferably 2 to 5 times mole relative to 1 mole of substituted phenylboronic acid compounds or substituted phenylboronic esters.

For effecting the reaction according to the present invention, it is satisfactory that for example, the predetermined amounts of substituted phenylboronic acid compounds or substituted phenylboronic esters, a 2-halogen-3,3,3-trifluoropropene compound, a base and a solvent are charged into a reactor; the catalyst is injected normally at −100 to 220° C., preferably at 0 to 120° C. while stirring; and the reaction is effected normally for 1 to 20 hours, preferably 3 to 15 hours or so.

From the reaction mixture after the completion of the reaction, a 2-(substituted phenyl)-3,3,3-trifluoropropene compound can be isolated by a combination of normal isolation purification means, for example isolation operations such as an extraction, a condensation, a distillation, a recrystallization or a column chromatography.

EXAMPLES

Hereinafter, the present invention is described more specifically referring to Examples, however, which should not be construed as limiting the scope of the present invention.

Example 1

95 mg (0.5 mmol) of 3,5-dichlorophenylboronic acid and 130 mg (0.75 mmol) of 2-bromo-3,3,3-trifluoropropene were dissolved in 3 mL of tetrahydrofuran and to the resultant solution, 2 mL of water, 138 mg (1.0 mmol) of potassium carbonate and 3.28 mg (0.005 mmol as palladium) of 1,3-bis(2,6-diisopropylphenyl)imidazol-2-ylidene(1,4-naphthoquinone)palladium(0)dimer were added, followed by stirring at 90° C. in an airtight container in a nitrogen atmosphere for 5 hours. After the reaction completion, the product was cooled and was analyzed by the high performance liquid chromatography. The product was identified using an LCMS (Liquid Chromatography Mass Spectrometry) or a GCMS (Gas Chromatography Mass Spectrometry). The main product was 2-(3,5-dichlorophenyl)-3,3,3-trifluoropropene and the area percentage of 2-(3,5-dichlorophenyl)-3,3,3-trifluoropropene was 94% as measured by the high performance liquid chromatography (detected using a UV detector at a wavelength of 254 nm).

Comparative Example 1

95 mg (0.5 mmol) of 3,5-dichlorophenylboronic acid and 130 mg (0.75 mmol) of 2-bromo-3,3,3-trifluoropropene were dissolved in 3 mL of tetrahydrofuran and to the resultant solution, 2 mL of water, 138 mg (1.0 mmol) of potassium carbonate and 3.51 mg (0.005 mmol as palladium) of dichloro-bis(triphenyl phosphine)palladium were added, followed by stirring at 90° C. in an airtight container in a nitrogen atmosphere for 5 hours. After the reaction completion, the product was cooled and was analyzed by the high performance liquid chromatography. The product was identified using an LCMS or a GCMS. The main product was 2-(3,5-dichlorophenyl)-3,3,3-trifluoropropene and the area percentage of 2-(3,5-dichlorophenyl)-3,3,3-trifluoropropene was 55% as measured by the high performance liquid chromatography (detected using a UV detector at a wavelength of 254 nm).

[Examples 2 to 7 and Comparative Examples 2 to 7]

The reaction was performed similarly as in Example 1 and Comparative Example 1 respectively, except that 3,5-dichlorophenylboronic acid was changed to boronic acids shown in Table 1. The resultant respectively corresponding 2-substituted phenyl-3,3,3-trifluoropropenes were identified using an LCMS or a GCMS and the area percentage of 2-substituted phenyl-3,3,3-trifluoropropene was measured by the high performance liquid chromatography (detected using a UV detector at the wavelength of 254 nm). However, in the cases of Example 5 and Comparative Example 5, the area percentage of 2-(substituted phenyl)-3,3,3-trifluoropropene was measured by the gas chromatography (detected using FID detector).

TABLE 1

| | Boronic acids | 2-Substituted phenyl-3,3,3-trifluoropropenes Structural formula | Area percentage |
|---|---|---|---|
| Example 2 | 3,5-dibromophenylboronic acid | 2-(3,5-dibromophenyl)-3,3,3-trifluoropropene | 74% |
| Comparative Example 2 | 3,5-dibromophenylboronic acid | 2-(3,5-dibromophenyl)-3,3,3-trifluoropropene | 39% |
| Example 3 | 3-chlorophenylboronic acid | 2-(3-chlorophenyl)-3,3,3-trifluoropropene | 84% |
| Comparative Example 3 | 3-chlorophenylboronic acid | 2-(3-chlorophenyl)-3,3,3-trifluoropropene | 79% |
| Example 4 | 3-acetamidophenylboronic acid | 2-(3-acetamidophenyl)-3,3,3-trifluoropropene | 91% |
| Comparative Example 4 | 3-acetamidophenylboronic acid | 2-(3-acetamidophenyl)-3,3,3-trifluoropropene | 81% |
| Example 5 | 2-methylphenylboronic acid | 2-(2-methylphenyl)-3,3,3-trifluoropropene | 90% |
| Comparative Example 5 | 2-methylphenylboronic acid | 2-(2-methylphenyl)-3,3,3-trifluoropropene | 67% |

TABLE 1-continued

| | Boronic acids | 2-Substituted phenyl-3,3,3-trifluoropropenes Structural formula | Area percentage |
|---|---|---|---|
| Example 6 | F₃CO-C₆H₄-B(OH)₂ (meta) | F₃CO-C₆H₄-C(=CH₂)CF₃ (meta) | 86% |
| Comparative Example 6 | F₃CO-C₆H₄-B(OH)₂ (meta) | F₃CO-C₆H₄-C(=CH₂)CF₃ (meta) | 69% |
| Example 7 | H₃CO-C₆H₄-B(OH)₂ (meta) | H₃CO-C₆H₄-C(=CH₂)CF₃ (meta) | 91% |
| Comparative Example 7 | H₃CO-C₆H₄-B(OH)₂ (meta) | H₃CO-C₆H₄-C(=CH₂)CF₃ (meta) | 76% |

[Examples 8 to 10]

The reaction was performed similarly as in Example 1 and Comparative Example 1 respectively, except that the catalyst, solvent and temperature were changed to those shown in Table 2. The resultants respectively corresponding 2(3,5-dichlorophenyl)-3,3,3-trifluoropropene were identified using an LCMS or a GCMS and the area percentage of 2-(3,5-dichlorophenyl)-3,3,3-trifluoropropene was measured by the high performance liquid chromatography (detected using a UV detector at the wavelength of 254 nm).

[Example 11]

1,3-bis-(2,6-diisopropylphenyl)imidazolium chloride (IPr.HCl, 0.005 mmol) and palladium acetate (0.005 mmol) were dissolved in 1 mL of tetrahydrofuran and the resultant solution was stirred for 15 minutes to prepare a catalyst solution. In another container, 95 mg (0.5 mmol) of 3,5-dichlorophenylboronic acid and 130 mg (0.75 mmol) of 2-bromo-3,3,3-trifluoropropene were dissolved in 2 mL of tetrahydrofuran and to the resultant solution, 2 mL of water and 138 mg (1.0 mmol) of potassium carbonate, and thereafter the above catalyst solution were added, followed by stirring at 90° C. in an airtight container in a nitrogen atmosphere for 5 hours. After the reaction completion, the product was cooled and was analyzed by the high performance liquid chromatography. The product was identified using an LCMS or a GCMS. The main product was 2-(3,5-dichlorophenyl)-3,3,3-trifluoropropene and the area percentage of 2-(3,5-dichlorophenyl)-3,3,3-trifluoropropene was 73% as measured by the high performance liquid chromatography (detected using a UV detector at a wavelength of 254 nm).

TABLE 2

| | Boronic acids | Catalyst | Solvent | Temperature | 2-Substituted phenyl-3,3,3-trifluoropropenes Structural formula | Area percentage |
|---|---|---|---|---|---|---|
| Example 1 | 3,5-Cl₂-C₆H₃-B(OH)₂ | ((IPr)Pd(NQ))₂ | THF/H₂O | 90° C. | 3,5-Cl₂-C₆H₃-C(=CH₂)CF₃ | 94% |

TABLE 2-continued

| | Boronic acids | Catalyst | Solvent | Temperature | 2-Substituted phenyl-3,3,3-trifluoropropenes Structural formula | Area percentage |
|---|---|---|---|---|---|---|
| Comparative Example 1 | 3,5-dichlorophenyl-B(OH)$_2$ | PdCl$_2$(PPh$_3$)$_2$ | THF/H$_2$O | 90° C. | 2-(3,5-dichlorophenyl)-3,3,3-trifluoropropene | 55% |
| Example 8 | 3,5-dichlorophenyl-B(OH)$_2$ | Pd(t-Bu$_3$P)$_2$ *1 | CH$_3$CN/H$_2$O | 60° C. | 2-(3,5-dichlorophenyl)-3,3,3-trifluoropropene | 85% |
| Example 9 | 3,5-dichlorophenyl-B(OH)$_2$ | (IPr)PdCl(allyl) *2 | CH$_3$CN/H$_2$O | 60° C. | 2-(3,5-dichlorophenyl)-3,3,3-trifluoropropene | 90% |
| Example 10 | 3,5-dichlorophenyl-B(OH)$_2$ | Aceto(2'-di-t-butylphosphino-1,1'-biphenyly-2-yl)palladium(II) *3 | CH$_3$CN/H$_2$O | 60° C. | 2-(3,5-dichlorophenyl)-3,3,3-trifluoropropene | 69% |
| Example 11 | 3,5-dichlorophenyl-B(OH)$_2$ | Pd(OAc)$_2$ + IPr•HCl | THF/H$_2$O | 90° C. | 2-(3,5-dichlorophenyl)-3,3,3-trifluoropropene | 73% |

Note)
*1 bis(tri-t-butylphosphine) palladium (0)
*2 Allylchloro(1,3-bis(2,6-di-isopropylphenyl) imidazoly-2-ylidene)palladium (II)
*3 Aceto(2'-di-t-butylphosphino-1,1'-biphenyly-2-yl)palladium (II)

[Example 12]

5 g (26.2 mmol) of 3,5-dichlorophenylboronic acid and 6.87 g (39.3 mmol) of 2-bromo-3,3,3-trifluoropropene were dissolved in 25 g of 1,4-dioxane and to the resultant solution, 10 g of water, 7.24 g (52.4 mmol) of potassium carbonate and 9.2 mg (0.013 mmol as palladium) of 1,3-bis(2,6-diisopropylphenyl) imidazol-2-ylidene(1,4-naphthoquinone)palladium (0) dimer were added, followed by heating to reflux at 90° C. in a nitrogen atmosphere for 5 hours. After the reaction completion, the product was cooled and to the mixture, 10 g of water and 20 g of ethyl acetate were added. The phases were separated and to the organic phase, 10 g of a saturated salt solution were added to separate the phases again. The solvent was distilled off under reduced pressure and the residue was purified by a distillation under reduced pressure to obtain 6.18 g of a fraction of 58 to 64° C./2 mmHg. This fraction was a colorless liquid of 2-(3,5-dichlorophenyl)-3,3,3-trifluoropropene. Yield: 97.8%.

$^1$H NMR (CDCl$_3$, Me$_4$Si, 300 MHz) δ 7.40 (t, J=2.0 Hz, 1H), 7.3-7.35 (m, 2H), 6.05 (m, 1H), 5.83 (m, 1H).

INDUSTRIAL APPLICABILITY

The process for the production according to the present invention is useful as a process for production of 2-(substituted phenyl)-3,3,3-trifluoropropene which is a useful compound as a production intermediate of pesticides, medicines, functional materials.

The invention claimed is:

1. A process for production of a 2-(substituted phenyl)-3,3,3-trifluoropropene compound or salt thereof, the compound being represented by the formula (7):

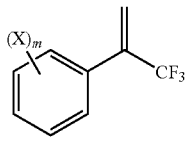
(7)

wherein X represents a halogen atom, a cyano group, a nitro group, —$SF_5$, a $C_1$-$C_6$ alkyl group, a $C_1$-$C_6$ haloalkyl group, a hydroxy ($C_1$-$C_6$) haloalkyl group, a $C_1$-$C_6$ alkoxy ($C_1$-$C_6$) haloalkyl group, a $C_1$-$C_6$ haloalkoxy ($C_1$-$C_6$) haloalkyl group, a $C_3$-$C_8$ halocycloalkyl group, —$OR^3$, —$OSO_2R^3$ or —$S(O)_rR^3$; and m represents an integer of 1 to 5 and when m represents 2 or more, each of Xs may be identical to or different from each other, wherein $R^3$ represents a $C_1$-$C_6$ alkyl group, a $C_1$-$C_6$ haloalkyl group or a $C_1$-$C_3$ haloalkoxy ($C_1$-$C_3$) haloalkyl group; and wherein r represents an integer of 0 to 2; the method comprising:

reacting a substituted phenylboronic acid or a substituted phenylboronic ester or a substituted phenylboronic acid salt represented by the formula (1):

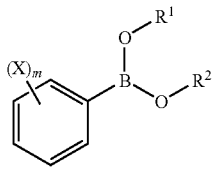
(1)

wherein X and m represent the same meanings as those above described;

wherein $R^1$ and $R^2$ may be identical to or different from each other and represent a hydrogen atom or an alkyl group, or a divalent hydrocarbon residue formed by $R^1$ and $R^2$ together in which the terminals of $R^1$ and $R^2$ are bonded to each other;

with a 2-halogen-3,3,3-trifluoropropene compound or salt thereof, the compound being represented by the formula (2):

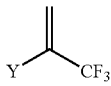
(2)

wherein Y represents a halogen atom,
in the presence of a complex catalyst represented by the formula (3):

wherein M represents as a central atom, a metal belonging to Group 10 on the elementary periodic table in an oxidation state number of 0 to 8;

wherein A represents a univalently or multivalently charged anion;

wherein b represents any integer of 1 to 3; a represents an integer produced by multiplying any integer of 1 to 5 by the above integer b; c represents 0 or represents an integer produced by multiplying an integer of 1 to 4 by the above b; n1 represents an integer of 1 to 6; and n2 represents an integer of 0 to 6;

wherein when a represents 2 to 15, each of Ls may be identical to or different from each other with proviso that all Ls do not represent simultaneously triphenylphosphine;

wherein G represents a unidentate or multidentate charged or uncharged ligand bonded to the central atom M;

wherein L is bonded as a ligand to the central atom M, and represents:

a phosphine compound represented by the formula (4):

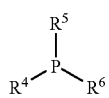
(4)

wherein each of $R^4$, $R^5$ and $R^6$ may be identical to or different from each other and represent a hydrogen atom, a $C_1$-$C_6$ alkyl group, a $C_3$-$C_{18}$ monocyclic or polycyclic cycloalkyl group or a $C_6$-$C_{14}$ aryl group which may be substituted by a substituent such as a di-($C_1$-$C_6$ alkyl) amino group, a $C_1$-$C_6$ alkoxyl group and an aryl group which may be substituted by a substituent such as a di-($C_1$-$C_6$ alkyl) amino group and a $C_1$-$C_6$ alkoxyl group, or a carbene represented by the formula (5):

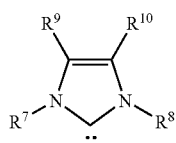
(5)

or by the formula (6):

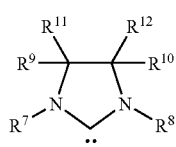
(6)

wherein each of $R^7$ and $R^8$ may be identical to or different from each other and represent a linear or branched $C_1$-$C_7$ alkyl group, a monocyclic or polycyclic $C_3$-$C_{18}$ cycloalkyl group or an aryl group having 6 to 14 carbon atoms which may be substituted by a substituent such as a linear or branched $C_1$-$C_7$ alkyl group, or a monocyclic or polycyclic $C_3$-$C_{18}$ cycloalkyl group;

wherein each of $R^9$, $R^{10}$, $R^{11}$ and $R^{12}$ may be identical to or different from each other, may be also a hydrogen atom, and represent a linear or branched $C_1$-$C_7$ alkyl group, a monocyclic or polycyclic $C_3$-$C_{18}$ cycloalkyl group, an aryl group having 6 to 14 carbon atoms which is optionally substituted by a linear or branched $C_1$-$C_7$ alkyl group, a linear or branched $C_1$-$C_7$ alkoxy group, or a linear or branched $C_1$-$C_7$ alkylthio group; and wherein $R^7$ and $R^9$, $R^8$ and $R^{10}$, $R^7$, $R^9$ and $R^{11}$, or $R^8$, $R^{10}$ and $R^{12}$ may form together a condensed ring.

2. The process for production according to claim 1, wherein the X represents a halogen atom or a $C_1$-$C_4$ haloalkyl group and m represents an integer of 1 to 3, and wherein when m represents 2 or 3, each of Xs may be identical to or different from each other.

3. The process for production according to claim 1, wherein at least one of the Ls in formula (3) represents a carbene represented by the formula (5) or the formula (6).

4. The process for production according to claim 1, wherein:
at least one of the Ls in formula (3) represents a carbene represented by the formula (5) or the formula (6);
each of $R^7$ and $R^8$ represents 2,4,6-trimethylphenyl group, 2,6-diisopropylphenyl group, 2,6-diisopropyl-4-methylphenyl group, an 1-adamantyl group, a tert-butyl group, a cyclohexyl group, a tolyl group, or a xylyl group; and
$R^9$, $R^{10}$, $R^{11}$ and $R^{12}$ each represent a hydrogen atom.

5. The process for production according to claim 1, wherein at least one of the Ls in formula (3) represents a phosphine compound represented by the formula (4) and at least one of $R^4$, $R^5$ and $R^6$ represents an adamantyl group, a norbornyl group, a tert-butyl group or a cyclohexyl group.

6. The process for production according to claim 2, wherein:
m in formula (7) represents an integer of 2 and two substituents represented by X in formulas (1) and (7) are located at a 3-position and a 5-position to the —$BOR_1$($OR_2$) in formula (1) or the trifluoropropenyl group of formula (7), as shown below in formulas (1') and (7'):

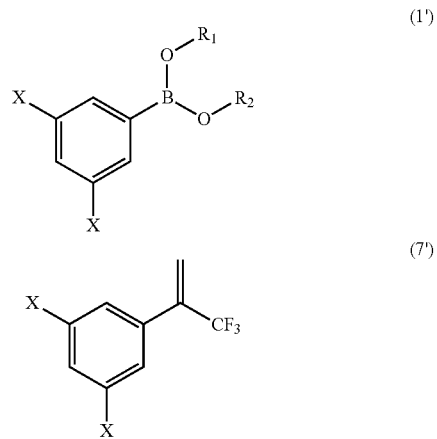

and each of the Xs in formulas (1') and (7') may be identical to or different from each other.

* * * * *